United States Patent
Sarkar

(10) Patent No.: US 7,915,406 B2
(45) Date of Patent: Mar. 29, 2011

(54) PROCESS FOR PREPARING A BENZOXAZINONE

(75) Inventor: Asim Kumar Sarkar, Danbury, CT (US)

(73) Assignee: Temsa International Inc., Newtown, CT (US)

( * ) Notice: Subject to any disclaimer, the term of this patent is extended or adjusted under 35 U.S.C. 154(b) by 313 days.

(21) Appl. No.: 12/159,999

(22) PCT Filed: Jan. 5, 2007

(86) PCT No.: PCT/EP2007/000158
§ 371 (c)(1),
(2), (4) Date: Sep. 29, 2008

(87) PCT Pub. No.: WO2007/007728
PCT Pub. Date: Jul. 12, 2007

(65) Prior Publication Data
US 2009/0030119 A1  Jan. 29, 2009

(30) Foreign Application Priority Data
Jan. 5, 2006 (EP) .................................. 06075016

(51) Int. Cl.
*C07D 265/06* (2006.01)
(52) U.S. Cl. ............................... 544/92; 544/93; 544/94
(58) Field of Classification Search .................... 544/92, 544/93, 94
See application file for complete search history.

(56) References Cited

U.S. PATENT DOCUMENTS

| 3,989,698 A | 11/1976 | Jacobs et al. |
| 4,446,262 A | 5/1984 | Okumura et al. |
| 2003/0096889 A1 | 5/2003 | Sarkar |

FOREIGN PATENT DOCUMENTS

| WO | WO9322300 | 11/1993 |

*Primary Examiner* — Kahsay T Habte
(74) *Attorney, Agent, or Firm* — Hoffman & Baron, LLP

(57) ABSTRACT

The invention relates to a method for preparing a benzoxazinone comprising reacting an isatoic anhydride with an acylating compound in the presence of an N-alkyl imidazole, to a method for preparing a photo-stabilised composition, comprising adding a benzoxazinone and to the use of a benzoxazinone as a light-absorber or as a stabiliser for a light-sensitive compound.

17 Claims, No Drawings

PROCESS FOR PREPARING A BENZOXAZINONE

This application is the U.S. National Phase of, and Applicants claim priority from, International Application Number PCT/EP2007/000158 filed 5 Jan. 2007 and European Patent Application bearing Serial No. EP 06075016.3 filed 5 Jan. 2006, which are incorporated herein by reference.

BACKGROUND OF THE INVENTION

The invention relates to a method for preparing benzoxazinone and to the use of the prepared benzoxazinone.

Benzoxazinones may be used for the stabilisation of polymers against the degradative effects of light, as described in U.S. Pat. No. 4,446,262 or U.S. Pat. No. 3,989,698. The described methods for preparing benzoxazinone result in a benzoxazinone of some noticeable undesirable properties, either imparting high degree of colour to clear plastics, which limits their use to certain applications, or having a high concentration of sodium ions.

U.S. patent application 2003/0096889 A1 describes a method for preparing benzoxazinones. The method uses the reaction of recrystallised isatoic anhydride (ISA) with an acylating compound in the presence of pyridine, preferably anhydrous pyridine. The method requires the recrystallisation of the ISA, in order to remove coloured contaminants from the ISA, which would otherwise contaminate the final product. The recrystallisation step adds to the complexity of the method. Also, recrystallisation results in loss of raw material, imparts extra costs (extra solvent, equipment) and is undesired from an environmental point of view (incineration).

It is an object of the invention to provide a novel method for preparing a benzoxazinone, that can be used as an alternative to known methods.

In particular it is an object of the invention to provide a method which overcomes one or more of the drawbacks from which known methods may suffer, as described above.

More in particular it is an object of the invention to provide a method for preparing a benzoxazinone which allows the preparation of a benzoxazinone with a low yellow index and/or a low sodium concentration, especially also if commercially available ISA, in particular technical grade ISA is used that is not further purified by recrystallisation or otherwise prior to reaction with the acylating compound.

It has now been found that a benzoxazinone can suitably be prepared in the presence of a specific amine.

DESCRIPTION OF THE INVENTION

Accordingly, the present invention relates to a method for preparing a benzoxazinone comprising reacting an isatoic anhydride with an acylating compound in the presence of an N-alkyl imidazole.

It has been found that also in the absence of recrystallising the ISA, even if it is only of technical grade and has a yellowish/brownish colour, a benzoxazinone can be prepared with an acceptable yield and quality (in terms of the colour and/or sodium ion concentration).

Besides, the inventor has realised that a amine suggested in the prior art, such as pyridine is an unpleasant (potentially unsafe) solvent to work with, compared to an N-alkyl imidazole.

The reaction conditions are not particularly critical and may be based upon the conditions described in U.S. application 2003/0096889, U.S. Pat. No. 4,446,262 or U.S. Pat. No. 3,989,698, of which the contents—in particular with respect to the reaction conditions—are herein incorporated by reference.

The method according to the invention is usually carried out a temperature of 150° C. or less. The temperature is usually at least 20° C. Preferably the temperature is in the range of 25-140° C., in particular in the range of 30-95° C.

In principle, any benzoxazinone may be prepared in accordance with the invention, in particular the benzoxazinones with a chemical structure described in U.S. application 2003/0096889 (see in particular paragraphs [0012]-[0022] and more in particular paragraph [0022]), U.S. Pat. No. 4,446,262 or U.S. Pat. No. 3,989,698 (see in particular formulas I and II in column 2, lines 16-68 and column 6, line 37 to column 7 line 68), of which the contents with respect to the benzoxazinones are herein incorporated by reference.

A method of the invention is in particular suitable for preparing a benzoxazinone represented by formula I

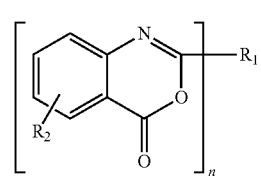

Formula I wherein n is generally 1, 2 or 3

$R_1$ may be a direct bond or a hydrocarbon residue which may have a valence of n which hydrocarbon residue may further contain an heteroatom and $R_2$ is usually hydrogen, halo, nitro, alkyl, alkoxy, or alkenyloxy.

In particular, $R_1$ may be a saturated or unsaturated organic radical having 1-30 carbon atoms. It may comprise one or more heteroatoms, for instance as substituent for one or more hydrogens The alkyl, alkoxy respectively alkenyloxy in $R_2$ usually comprises 1-30 carbon atoms. It may comprise one or more heteroatoms, for instance as substituent for one or more hydrogens. In particular, the number of carbon atoms may be in the range of 1 to 8.

The skilled person will know to choose a suitable isotoic anhydride (ISA), depending on the desired benzoxazinone, in particular in view of the above cited prior art. With respect to suitable isotoic anhydride the parts of U.S. application 2003/0096889, U.S. Pat. No. 4,446,262 and U.S. Pat. No. 3,989,698 (see in particular column 3, lines 38-58) relating to this compound are herein incorporated by reference.

The acylating compound is usually selected from the group consisting of carboxylic acid anhydrides, amino carboxylic acids and acyl halides. Suitable examples are e.g. known form the above cited prior art.

With respect to a suitable acylating compound the parts of U.S. application 2003/0096889 (see in particular paragraphs [0035] and [0036]), U.S. Pat. No. 4,446,262 and U.S. Pat. No. 3,989,698 (see in particular column 2, line 66 to column 3, line 38) relating to these compounds are herein incorporated by reference.

A method according to the invention may suitable be carried out with a technical grade isatoic anhydride, in particular such compound with a brownish or yellowish colour, without needing purification to remove colour.

As N-alkyl-imidazole, preferably a commercially readily available N-alkyl-imidazole is used. Suitable examples include N—C1-C8 alkyl imidazoles. In a preferred method at least one N-alkyl-imidazole is used selected from the group consisting of N-methyl imidazole, N-ethyl imidazole, N-propyl imidazole and N-butyl imidazole.

The ratio of N-alkyl imidazole to isatoic anhydride may be chosen in wide limits.

In principle, a catalytic amount of N-alkyl imidazole suffices. It has been found advantageous to use N-alkyl imidazole or a mixture thereof as a solvent or suspending liquid for the reagents. In a preferred embodiment N-alkyl imidazole is the major solvent or suspending liquid, for instance making up more than 50 wt. % of the total solvent/suspending liquid. It has been found that thus a high yield can be obtained.

Alternatively another solvent or suspending liquid is used as the major solvent or suspending liquid. In particular another organic solvent/suspending liquid may be used, for instance a cycloalkane, e.g. methylcyclohexane, an alkane amide, such as dimethylformamide, or another organic solvent or suspending liquid that does not react with the other components, in particular not with the acylating agent may be used. The use of a further solvent or suspending liquid may be desirable for economic reasons.

Also when using a further solvent or suspending liquid as the major solvent or suspending liquid, good yields can be obtained.

Particularly good results have been achieved with dimethylformamide, which has been found to be useful to from an economic view point, whilst maintaining a high yield.

If a solvent or suspending liquid is used next to the N-alkyl imidazole, it preferably makes up at least 50 wt. % of the total solvent/suspending liquid including the N-alkyl imidazole, more preferably at least 80 wt. % of the total solvent/suspending liquid. The upper limit is determined by the amount of N-alkyl imidazole. The amount may in particular be up to 99 wt. % of the total solvent/suspending liquid, more in particular up to 95 wt % or up to 90 wt. %.

In view of the reaction rate, weight to weight the ratio is preferably at least 0.1, in particular at least 0.5. In an embodiment, the ratio is at least 0.8, in particular at least 5, in particular in case the N-alkyl imidazole is the sole or the major solvent. This facilitates stirring during the reaction, in case imidazole is the sole or major solvent. For practical reasons, the ratio is usually 30 or less, in particular 20 or less. The weight to weight ratio is preferably 15 or less, in particular 12 or less.

In terms of a mole to mole ratio of N-alkyl imidazole to isoatoic anhydride, the ratio is preferably at least 0.2, more preferably at least 1. For practical reasons it is usually up to 60, in particular up to 40. Preferably the ratio is 30 or less, in particular 24 or less. Good yields have also been obtained at a lower mole to ratio, in particular of less than 10 less. For a good yield at a relatively low cost, a ratio of up to about 5, in particular of about 1-2 may be used, especially in case the N-alkyl imidazole is used in combination with a further solvent or suspending agent, such as dimethylformamide or the like.

In practice, the isatoic anhydride and acylating compound are usually present in a molar ratio in the range of 0.5 to 3, preferably in a range of 0.7 to 2.6, in particular 0.9-2.2. Preferably, (about) stoichimetrical amounts of both components are used; in case the acyl compound has one functional group the ratio is preferably in a range of 0.7-1.3, in particular in a 0.9 to 1.1. In case the acyl compounds has two functional groups the ratio is preferably 1.3-2.6, in particular 1.8 to 2.2.

The invention further relates to a method for preparing a photo-stabilised composition, comprising adding a benzoxazinone prepared according to the invention to a light-sensitive compound, in particular a polymer.

The preparation of such a composition may be done by applying the benzoxazinone to the light-sensitive compound. The benzoxazinone may be made prior to forming an article from the compound (e.g. by mixing) or thereafter. The amount of benzoxazinone may be in the range of 0.05-5 parts per 100 parts of the light-sensitive compound. The benzoxazinone may in particular to protect a polyester, a polyamide, a polycarbonate, a polyolefin a polyethoer, a polysulfon, a phenolformaldehyde resin, melamine resin, polyurethane resin, urea resin, epoxi resin or unsaturated polyester resin. The preparation may be based on the methodology described in U.S. Pat. No. 4,446,262, whereof the contents relating to the methods of protecting a product from ultraviolet light are incorporated herein by reference.

Further, the invention relates to the use of a benzoxazinone prepared according to any one of the claims 1-9 as a light-absorber or as a stabiliser for a light-sensitive compound, in particular in an optical lens or other application wherein high transparency of the product is desired or needed.

The invention will now be illustrated by the following example.

EXAMPLE 1

125 gm of Isatoic anhydride (ISA)-Tech. grade* was dissolved in 1475 gm of N-methyl imidazole (NMI), the mixture heated to 60° C. and 91.3 gm of terephthaloyl chloride (TPC) was added during a period of 30 minutes under good agitation. The temperature was raised to 120-130° C. and held at this temperature for a further 4 hours. The mixture was cooled to 30° C. and the precipitate was filtered. The precipitate was re-slurried in 400 ml. of isopropyl alcohol (99%) (IPA) and washed 3 times with portions of 150 ml. of IPA. The precipitate so obtained was re-slurried in 450 gm of NMI heated to 95° C., held for 30 min. under agitation and filtered. The wet cake was washed with hot IPA and dried under vacuum (20 mm) at 80° C.

*technical grade isatoic anhydride (sold in Europe and U.S.A. by PMC corporat, U.S.A. and Chromogenia S.A. of Barcelona Spain.) is brown to light t brown in colour and is has a purity >98.5%

The product -[2,2-p-phenylenebis(3,1-benzoxazinone-4-one)] 107 gm was a white powder and 98.5% pure by HPLC assay. The product was extracted with dimethylformamide (DMF) and the extracted liquor was found to have a colour value of <50 APHA.

EXAMPLE 2A 32.6 gm of Isatoicanhydride (ISA) (0.2 mol.) was dissolved in a mixture of Dimethyl formamide (DMF) (150 ml.) and N-methylimidazole (NMI) 18.2 gm (0.22 mol.) at 86-90° C. 21.7 gm (0.107 mol.) of Terephthaloylchloride (TPC). TPC was added at this temperature to the mixture under stirring over a period of 30 minutes. The reaction mixture temperature was raised to 110-120° C. and stirred for 4 hrs. The mixture was cooled to 20-25° C. and stirred for a further 2 hrs. The product was then filtered and washed on the filter with 150 ml. of methanol, and dried at 60° C. Yield of 2,2-p-phenylene-bis[4H-3,1-benzoxazinone-4-one]/(PBBOX) was 29.8 gm. (81%).

EXAMPLE 2B (REFERENCE EXAMPLE)

Reaction of Isatoicanhydride (0.2 mol), DMF 150 ml, Pyridine (0.22 mol), TPC (0.107 mol) under the above reaction conditions gave yield of only 45.9% of PBBOX.

EXAMPLE 2C (REFERENCE EXAMPLE)

Replacement of NMI by triethylamine under otherwise the same conditions as in Example 2A resulted in hardly any yield of PBBOX at all.

The invention claimed is:
1. Method for preparing a benzoxazinone of formula I

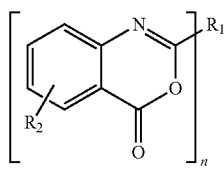

wherein n is 1, 2, or 3;
$R_1$ is a saturated or unsaturated radical having 1-30 carbon atoms, wherein
one or more carbon atom may be substituted for a heteroatom; and
$R_2$ is hydrogen, halo, nitro, alkyl, alkoxy, or alkenyloxy;
the method comprising reacting an isatoic anhydride with an acylating compound in the presence of an N-alkyl imidazole.

2. Method according to claim 1, wherein the N-alkyl imidizole is selected from N-methyl imidazole, N-ethyl imidazole, N-propyl imidazole, N-butyl imidazole, and combinations thereof.

3. Method according to claim 1, wherein the weight to weight ratio of N-alkyl imidazole to isatoic anhydride is in the range of 0.1 to 30.

4. Method according to claim 1, wherein the reaction is carried out in a liquid comprising a solvent or suspending liquid other than the N-alkyl imidazole.

5. Method according to claim 4, wherein the concentration of the other solvent or suspending liquid is at least 50 wt. % based on the total amount of the solvent/suspending liquid including the N-alkyl imidazole.

6. Method according to claim 1, wherein the isatoic anhydride and acylating compound are dissolved or suspended in the N-alkyl imidazole or in a liquid comprising the N-alkyl imidazole as the major solvent or suspending liquid.

7. Method according to claim 1 wherein the isatoic anhydride and acylating compound are present in a molar ratio in the range of 0.7 to 2.6.

8. Method according to claim 1, wherein the acylating compound is selected from the group consisting of carboxylic acid anhydrides, amino carboxylic acids and acyl halides.

9. Method according to claim 1, wherein the isatoic anhydride is a technical grade isatoic anhydride.

10. Method according to claim 1, wherein the temperature is in the range of 20 to 150 ° C.

11. Method according to claim 3, wherein the weight to weight ratio of N-alkyl imidazole to isatoic anhydride is in the range of 0.8 to 20.

12. Method according to claim 11, wherein the weight to weight ratio of N-alkyl imidazole to isatoic anhydride is in the range of 5 to 15.

13. Method according to claim 4, wherein said solvent or suspending liquid is dimethylformamide.

14. Method according to claim 7 wherein the isatoic anhydride and acylating compound are present in a molar ratio in the range 0.9 to 2.2.

15. Method according to claim 14 wherein the isatoic anhydride and acylating compound are present in a molar ratio in the range of 0.9 to 1.1.

16. Method according to claim 10, wherein the temperature is in the range of 25- 140° C.

17. Method according to claim 16, wherein the temperature is in the range of 30-95° C.

* * * * *